United States Patent
Hardman et al.

Patent Number: 4,657,887
Date of Patent: Apr. 14, 1987

[54] CATALYST COMPOSITION FOR THE PREPARATION OF ALCOHOLS

[75] Inventors: Harley F. Hardman, Lyndhurst; Terry J. Mazanec; John G. Frye, Jr., both of Solon, all of Ohio

[73] Assignee: The Standard Oil Company, Cleveland, Ohio

[21] Appl. No.: 754,879

[22] Filed: Jul. 15, 1985

[51] Int. Cl.$^4$ .................. B01J 21/04; B01J 23/02; B01J 23/12; B01J 23/72
[52] U.S. Cl. .................... 502/303; 502/304; 502/318; 502/324; 502/331; 502/340; 502/341; 502/342; 502/343; 502/345; 502/346; 518/713
[58] Field of Search ............. 502/346, 303, 318, 331, 502/342, 304, 324, 340, 341, 343, 345; 518/713

[56] References Cited

U.S. PATENT DOCUMENTS

| | | | |
|---|---|---|---|
| 2,787,628 | 4/1957 | Himmler et al. | 518/714 |
| 4,298,354 | 11/1981 | Hardman et al. | 44/56 |
| 4,451,579 | 5/1984 | Lemanski et al. | 502/318 X |

FOREIGN PATENT DOCUMENTS 608361 1/1935 Fed. Rep. of Germany .
229715 2/1925 United Kingdom .

*Primary Examiner*—W. J. Shine
*Attorney, Agent, or Firm*—Larry W. Evans; David J. Untener; Raymond F. Keller

[57] ABSTRACT

A catalyst composition containing alkali metal or alkaline earth metal uranate suitable for the conversion of mixtures of carbon monoxide and hydrogen has the formula $$Cu_a U M_b A_c O_x$$

where M is one or more metals selected from the group consisting of Th, Pd, Mn, Cr, Fe, Co, Zn, Ce, V, Ru, Rh, Al, Re, Os, Pt, Ir, Ag, Ti, La and Zr, A is an alkaline or alkali earth metal and a is from 0.01 to 5.0;
b is from 0 to 5.0 with the proviso that when M is Th the value of b is less than 1;
c is a number up to 5.0 selected so that the catalyst composition contains more than 2 percent by weight of Metal A;
x is a number such that the valence requirements of the other elements for oxygen are satisfied.

The catalyst composition can be used to prepare an alcohol composition containing at least 30 percent by weight of methanol, the remainder of said composition comprising higher alcohols, the distribution of which on a methanol-free basis is $C_2$–10 to 90 weight percent
$C_3$–15 to 60 weight percent
$C_4$–0.5 to 35 weight percent
$C_5$–0 to 15 weight percent
$C_6$–0 to 15 weight percent and wherein the percent of $C_3$ is at least 1.25 times the percent of $C_4$.

7 Claims, No Drawings

4,657,887

CATALYST COMPOSITION FOR THE PREPARATION OF ALCOHOLS

TECHNICAL FIELD

This invention relates to a catalyst composition containing copper and uranium and to a process for the conversion of mixtures of carbon monoxide and hydrogen to alcohols using said catalyst composition.

BACKGROUND OF THE INVENTION

The conversion of mixtures of carbon monoxide and hydrogen to alcohols has been previously described and a variety of metal catalysts have been proposed for this purpose.

For example, U.S. Pat. No. 2,061,470 describes the production of methanol using as catalyst the reaction product of a fused mixture of copper oxide and manganese oxide or copper oxide and zinc oxide and an oxide selected from the group consisting of chromium, vanadium, zirconium, aluminum, magnesium, titanium, thorium, silicon and cerium.

U.S. Pat. No. 4,298,354 describes an oxide complex catalyst containing copper and thorium and having the formula $Cu_aThM_bA_cO_x$ wherein M is one or more of Ca, Mo, Rh, Mn, Pt, Ce, Cr, Zn, Al, Ti, La, V, U, Ru, Re and Pd, A is an alkali metal and wherein a is 0.5 to 2.5; b is 0.01 to 1.0; c is 0.05 to 0.9 and x is a number such that the valence requirements of the other elements for oxygen is satisfied.

Catalysts containing copper and uranium have been described in U.S. Pat. No. 4,375,425 as being effective for the water gas shift reaction i.e. $CO+H_2O=CO_2+H_2$. The catalysts described are said to consist essentially of an alkali metal promoted partially reduced mixture of at least one copper uranate of formula $CuUO_4$ or $CuU_3O_{10}$ and at least one oxide of copper of formula $CuO$ or $Cu_2O$. The amount of alkali metal disclosed is from 0.01 to 2 weight percent of the catalyst.

U.S. Pat. No. 4,237,063 describes catalysts for making alcohols from carbon monoxide and hydrogen containing alumina and a metal cyanocuprate of formula $A_xB_y[Cu(CN)_4]$ where A and B can be selected from a list of metals which includes uranium and alkali and alkaline earth metals. There is no disclosure of the specific combination of copper, uranium and alkali metal and none of the catalysts described contain chemically bound oxygen.

U.S. Pat. No. 4,312,955 describes catalysts for the conversion of carbon monoxide and hydrogen to methanol which contain lanthanum rhodate which can be substituted with metal cations such as uranium and copper. However, there is no disclosure of the presence of alkali metal or alkaline earth metal.

SUMMARY OF THE INVENTION

According to one aspect of the present invention a catalyst composition containing alkali or alkaline earth metal uranate or mixture thereof suitable for the conversion of mixtures of carbon monoxide and hydrogen to alcohols has the formula $Cu_aUM_bA_cO_x$ where M is one or more metals selected from the group consisting of Th, Pd, Mn, Cr, Fe, Co, Zn, Ce, V, Ru, Al, Re, Os, Pt, Ir, Ag, Ti, La and Zr, A is an alkali or alkaline earth metal or mixture thereof and a is from 0.01 to 5.0 preferably from 0 to 0.5;

b is from 0 to 5.0 with the proviso that when M is Th the value of b is less than 1;

c is a number up to 5.0 preferably from 0.5 to 2.0 selected so that the catalyst composition contains more than 2 percent by weight of Metal A;

x is a number such that the valence requirements of the other elements for oxygen are satisfied.

The catalysts of the present invention are distinguished from those described in U.S. Pat. No. 4,298,354 referred to above in that they contain alkali metal or alkaline earth metal uranate. Further, when thorium is present, the atomic ratio of U to Th is always greater than 1.

This difference in composition gives the catalysts of the present invention an important advantage over those described in U.S. Pat. No. 4,298,394 in that they produce a higher ratio of $C_3$ to $C_4$ alcohols. This ratio is at least 1.25:1 on a weight basis and is important because it is not desirable, when forming alcohols from syn gas, that alcohols of carbon number 4 and higher form a significant proportion of the product. The reason for this is that for each molecule of carbon monoxide used in building the carbon chain, an atom of oxygen must be discarded either in the form of water or carbon dioxide with consequent loss of feed.

Further, the catalysts of the present invention are distinguished from those described in U.S. Pat. No. 4,375,425 referred to above in that they contain amounts of alkali metal in excess of 2 percent by weight and, as shown by x-ray diffraction contain alkali metal or alkaline earth metal uranate.

According to a further aspect of the present invention a process for the conversion of a mixture of carbon monoxide and hydrogen to alcohols comprises contacting the mixture under alcohol forming conditions at elevated temperature and pressure with a catalyst composition containing alkali metal or alkaline earth metal uranate or a mixture thereof having the formula $Cu_aUM_bA_cO_x$ where M is one or more metals selected from the group consisting of Th, Pd, Mn, Cr, Fe, Co, Zn, Ce, V, Ru, Al, Re, Os, Pt, Ir, Ag, Ti, La and Zr, A is an alkali or alkaline earth metal or mixture thereof and a is from 0.01 to 5.0 preferably from 0.5 to 2.5;

b is from 0 to 5.0 with the proviso that when M is Th the value of b is less than 1;

c is a number up to 5.0 selected so that the catalyst contains more than 2 percent by weight of Metal A;

x is a number such that the valence requirements of the other elements for oxygen are satisfied.

In stating that the valence requirements of the other elements for oxygen are satisfied, we do not intend to exclude catalysts where copper is present in an elemental or zerovalent state, provided there is some chemically bound oxygen in the catalyst.

The above formula is not intended to be limited to catalysts containing only the elements specified for M and A in combination with copper, but includes the optional presence of other elements in addition to those specified.

DETAILED DESCRIPTION OF THE INVENTION

As stated above, the catalyst composition contains more than 2 percent by weight of the metal A. Preferably, the catalyst composition contains at least 5 percent by weight of the metal A. Although there is no upper limit, it is not convenient to exceed 20 or 15 percent by weight. Also as stated above, when thorium is present the atomic ratio of U to Th is greater than 1. Preferably, this ratio is greater than 2.

The catalyst composition may be prepared by mixing compounds of the metals in solution and precipitating the metals from solution (by the addition of a precipitating agent) in the form of their oxides or a form thermally decomposable to their oxides. A method similar to that described in U.S. Pat. No. 4,298,354 may be employed, except that in the present case a soluble compound of uranium is employed.

The technique described in U.S. Pat. No. 4,298,354 involves precipitation from an aqueous solution and while this is generally very satisfactory for most metals it has been found that certain uranium compounds have a high solubility in water, even at pH values above 9, and uranium is for this reason not always easily precipitated with the other metals.

It is therefore preferred to precipitate the metals from a polar organic solvent.

The polar organic solvent can be a ketone such as acetone, an ester such as methyl acetate, an ether such as tetrahydrofuran or an alcohol such as ethanol.

The precipitation of the metals from the solution in the polar organic solvent is conveniently effected by mixing the solution with a solution of the precipitating agent also in a polar organic solvent.

The term polar organic solvent as used herein is intended to mean a solvent containing at least 50 percent by volume of a polar organic solvent. Water can be present but desirably comprises less than 40 percent by volume of the total and preferably less than 10 percent. Preferably, the solvent consists essentially of the polar organic solvent which is preferably an alcohol or mixture of alcohols.

Preferred alcohols are $C_1$ to $C_{10}$ alcohols such as methanol, ethanol, n propanol, i-propanol, n butanol, i butanol, t-butanol, pentanols, hexanols, ethylene glycol, propylene glycol, glycerol or a mixture of these. Methanol is preferred. Small amounts of esters, ethers, alkenes, aromatics, or other solvents can also be present.

The metal compounds dissolved in the polar organic solvent can conveniently be salts such a nitrates, sulfates, halides, phosphates, acetates, other carboxylates or the like. Nitrates are preferred.

The precipitating agent can be a base such as an alkali or alkaline earth metal or ammonium hydroxide, carbonate or bicarbonate or mixture thereof.

The temperature at which the precipitation is effected can vary widely but is conveniently from 10° to about 40° C. The order of addition is not critical.

The calcination is effected to decompose any thermally decomposable compounds especially salts to form the oxide and comprises heating in air to, for example, 250° to 750° C., preferably 300° to 450° C. for a sufficient period of time to decompose the compounds and form the oxides. Usually the duration of the calcination is from 1 to 6 hours.

Where an anion or anions other than oxide remains in the calcined solids then the calcined solids are treated to remove the anion prior to the use of the catalyst since the presence of anions tends to reduce the activity of the catalyst. The nature of the anion will depend on the metal salts from which the catalyst was precipitated since the source of the anion is the conterion of the metal in the salt used and may be, for example, chloride, nitrate, acetate or phosphate and the like.

The removal of these ions for example chloride, nitrate, acetate and phosphate is conveniently effected by washng with water or other suitable solvent.

Alternatively, the anions may, in suitable cases, be removed by gentle reduction, for example, nitrate and acetate can be removed by gently heating in a stream of a reducing gas such as carbon monoxide or hydrogen. The reduction conditions should be mild in order to avoid an exothermic reaction resulting in the catalyst forming a fused and inactive mass.

The washed catalyst can then be impregnated with an aqueous solution of an alkaline or alkaline earth metal ions for example, lithium, sodium, potassium, rubidium, cesium, beryllium, magnesium, calcium, strontium or barium to increase the loading of metal A. Suitable compounds for dissolving the water to effect the impregnation are hydroxides, carbonates or bicarbonates. Conveniently up to 10 percent by weight of additional metal A may be added by impregnation.

Preferably the catalyst is formed into pellets by incorporation of a binding agent and pressing in a pellet press. Suitable binding agents include graphite, titanium dioxide, thorium dioxide, alumina, or zirconium dioxide. These agents may be used as a colloidal dispersion. Conveniently 1 to 10 percent, preferably 3 to 5 percent of graphite is useful as a binding agent.

The catalyst can be subjected to a reductive activation treatment before use by contacting with a suitable reducing gas such as hydrogen at a temperature suitable for at least partial reduction of one or more of the metal oxides to a reduced form. Conveniently a dilute stream of hydrogen is nitrogen (15 percent $H_2$, 85 percent $N_2$) is used and the catalyst is charged to a stainless steel tube placed in a programmable furnace capable of slowly raising the temperature from ambient to the highest temperature of the reduction, preferably 250° C. or the temperature at which the catalyst will be used in the subsequent reaction to form alcohols. The reduction is preferably accomplished at about atmospheric pressure although elevated pressures up to about 100 atmospheres can be used.

The feed and process conditions for the production of alcohols are as follows. Although synthesis gas is a preferred reactant, any other gas composed primarily of hydrogen and carbon monoxide and having an $H_2$ to CO ratio of about 1:10 to about 10:1, preferably about 1:3 to about 3:1, can be employed. The gaseous reactants should contain as little sulfur compounds as possible since sulfur is a known poison for copper containing catalysts. Preferably, the gaseous reactants are essentially sulfur-free.

The contact time of the reactants with the catalyst is not critical but should be below about 200 seconds and preferably between about 5 and 100 seconds.

The reaction pressure should normally be in the range of about 150 to about 4000 psig, preferably about 750 to about 1000 psig. Although there is no real upper limit to the reaction pressure, pressures higher than about 1500 psig or 2000 psig are normally not employed because of the high expense involved. It is preferable to operate at at least about 500 psig because formation of alcohols is favored at higher pressures.

The reaction temperature should be maintained in the range of about 100° to about 500° C., preferably about 200° to about 400° C., and more preferably about 250° to about 325° C.

The space velocity of the gaseous reactant is not critical but should be about 1000 to about 100,000, preferably about 2000 to about 20,000 liters of gaseous reactant per liter of catalyst per hour.

The process of the present invention yields alcohol compositions containing methanol and significant amounts of higher alcohols usually having 2 to about 8, preferably 2 to about 6 carbon atoms suitable for addition to gasoline. Normally, the alcohol compositions contain at least 30 percent by weight of methanol, although higher amounts of methanol may be included in the product if reaction temperature is too low or if the catalyst contains additional elements fostering the generation of higher amounts of methanol than normal.

The portion of the alcohol product other than methanol is usually a mixture composed primarily of 2 to about 6 carbon atom alcohols. The distribution of $C_2$-$C_6$ alcohols on a methanol-free basis is usually:

$C_2$-about 10 to about 90 percent
$C_3$-about 15 to about 60 percent, preferably about 25 to about 55 percent
$C_4$-about 0.5 to about 35 percent, typically, about 8 to about 30 percent
$C_5$-about 0 to about 15 percent
$C_6$-about 0 to about 15 percent.

The above-indicated percentages are by weight and based on the weight of the total amount of alcohols in the product having two or more carbon atoms. These alcohols are composed almost completely of isoalcohols and normal alcohols with the iso to normal ratio being in the range of about 0.01 to about 20. Preferably, substantially no tertiary alcohols are present.

The product alcohol mixtures of the present invention are useful in expanding gasoline. They can be mixed with gasoline in amounts up to about 25 percent by weight of the gasoline/alcohol mixture. Furthermore, the mixed alcohol products of the present invention can be mixed with any type of gasoline be it substantially all paraffinic such as alkylate or highly aromatic. Moreover, if the product alcohol mixtures employed have no more than about 85 percent by weight methanol, the resulting gasoline/alcohol mixture can tolerate significant amounts of water without phase separation.

Preferably, the alcohol mixtures produced in accordance with this invention contain not more than about 85 percent methanol, although those containing in excess of this figure for example up to about 95 percent methanol or more, can be used for addition with gasoline if such mixtures are blended with higher alcohols to provide a mixture with an overall methanol level of about 85 percent or less. These alcohol mixtures can be distilled to remove a sufficient amount of methanol to provide a mixture with a methanol level of about 85 percent or less.

In order to further illustrate the catalytic composition and process of the present invention, the following examples are provided. In the following examples as well as throughout the specification and claims, all parts and percentages are by weight and all temperatures are in degrees centigrade unless otherwise indicated.

SPECIFIC EMBODIMENTS

The invention is illustrated by the following Examples.

Example 1 Preparation of Catalyst (a) Precipitation from Methanol and Calcination The weights of reactants were chosen to correspond to a formula of $Cu_{0.75}UAl_{0.3}K_xO_y$.

(a) 50 g of $Cu(NO_3)_2.2\frac{1}{2}H_2O$; 144 g of $U(NO_3)_2O_2.6H_2O$ and 32 g of $Al(NO_3)_3.9H_2O$ were dissolved in 2 liters of methanol. A 2 molar solution of potassium hydroxide in methanol was added to the mixture over a period of about one hour until the pH was 9.5. A 2 molar nitric acid solution was then added to the mixture until the pH was 7.0. The mixture was then vacuum filtered and the filter cake reslurried with 300 ml of methanol and vacuum filtered again. This was repeated until the filter cake had been washed three times. The filter cake was then placed in an oven at room temperature and slowly heated to 400° C. and this temperature maintained for 2 hours.

The calcined solid contained 6.2 percent copper, 30 percent uranium, 1.0 percent aluminum and 25 percent potassium all percentages being by weight based on the total weight of solid corresponding to a formula of $Cu_{0.76}UAl_{0.29}K_{5.1}O_y$. The surface area was 0.41 m$^2$/g as determined by nitrogen absorption.

(b) Washing to Remove Anions and Impregnation with Potassium

The solid was placed in a stainless steel beaker with about one liter of water and stirred vigorously for 1½ days to effect washing. The solid after that time was a fine powder which was then vacuum filtered through a medium glass frit and additionally washed with three 100 ml portions of distilled water while still on the frit. The solid was then dried in an oven at 110° C. overnight and then impregnated with an aqueous potassium hydroxide solution made by dissolving 1.91 g of 85 percent potassium hydroxide in enough water to make 18 ml of total solution vacuum. Calculated so as to add 3 percent by weight of potassium to the catalyst. The weight of solid was 36.46 g. Following impregnation the solid was redried, then pelletized with 3 percent by weight of graphite and sieved to a 10-30 mesh fraction. The finished catalyst contained 9.9 percent copper
53 percent uranium
2.6 percent aluminum
8.2 percent potassium All percent being by weight of the catalyst. The surface area was 27.1 m$^2$/g determined by nitrogen absorption.

The purpose of the washing was to remove anions such as nitrate remaining from the precipitation step. The washing had the effect of additionally removing potassium, so that even though 3 percent of potassium was added by impregnation, the potassium content of the impregnated solid was much lower (8.2 percent) than the solid before washing (25 percent). The increase in surface area demonstrates that the washing removes material from the pores of the catalyst.

The product was examined by x-ray diffusion and found to contain potassium uranate.

Example 2 Preparation of Catalyst (a) Precipitation from Methanol and Calcination The proportions of reactants were chosen to correspond to a formula $Cu_{0.75}UAl_{0.3}K_xO_y$. 50 g of $Cu(NO_3)_2.2\frac{1}{2}H_2O$ (0.215 mole of copper), 144 g of $UO_2(NO_3)_2.6H_2O$ (0.287 mole of uranium), and 32 g of $Al(NO_3)_3.9H_2O$ (0.0853 mole of aluminum) were dissolved in 2 liters of methanol at room temperature. While vigorously stirring the solution, enough 2 molar potassium hydroxide in methanol was added by slow dropwise addition to bring the pH to 7.0. The precipitate was light green in color and was vacuum filtered, then washed once by reslurrying with 2 liters of absolute methanol and refiltering. The filter cake was then dried and calcined in one step by heating as follows: 25° C. to 400° C. at 1° C. per minute and then held at 400° C. for 2 hours and then allowed to cool to room temperature.

(b) Washing to Remove Anions and Impregnation with Potassium

The calcined solid, of mottled brown and yellow appearance was washed by stirring with 1 liter of distilled water for about 12 hours and was then vacuum filtered with a medium glass frit. The solid was washed a further three times while on the frit with 50 ml portions of distilled water and then dried overnight at 110° C. At this stage the material contained 11 percent copper, 56 percent uranium, 2.0 percent aluminum and 5.6 percent potassium. The surface area was 48.9 m²/g. The product was examined by x-ray diffraction and found to contain potassium uranate. This material was then impregnated with a further 3 percent by weight of potassium (as KOH) redried, then pelletized with 3 percent by weight of graphite. The finished catalyst contained 10 percent copper, 54 percent uranium, 1.8 percent aluminum, and 8.7 percent potassium all by weight of the catalyst corresponding to a formula of $Cu_{0.69}UAl_{0.29}K_{1.0}O_y$. The surface area was 17.82 m²/g.

Example 3 Preparation of Catalyst

The weights of reactants were chosen to correspond to the formula $Cu_{0.75}UAlK_xO_y$.

70 g of the solid prepared in part (a) of Example 1 were stirred vigorously with 250 ml of water for one hour. The resulting slurry was vacuum filtered using a medium glass frit Buchner filter, then washed three more times with 25 ml portions of distilled water. The filter cake was dried in an oven overnight at 100° C. The dried filter cake contained 11 percent copper, 58 percent uranium, 2.0 percent aluminum and 7.3 percent potassium corresponding to a formula of $Cu_{0.71}UAl_{0.30}K_{0.76}O_y$. The product was examined by x-ray diffraction and found to contain potassium uranate. The product was pelletized with 3 percent by weight of graphite, and the pellets broken up to yield a 10–30 mesh fraction.

In the following examples a 20.0 cc sample of the catalyst was loaded into a reactor and reduced by programmed heating under 1.8 SLPM of a 1:5 volume ratio of hydrogen and nitrogen to a final temperature of 250° C. The catalyst was allowed to cool and the reactor was pressured to the desired pressure with synthesis gas (composition indicated in example) and heated by a programmed heating procedure under a flow of the synthesis gas to the desired reaction temperature. The liquid products were collected and analyzed by gas chromatography. The results are summarized in the following tables in which Tables 1–3 give the reaction conditions and yields of liquid product and Table 4 gives an analysis of the liquid product in weight percent in a methanol-free basis.

The term "higher alcohols" means alcohols containing two or more carbon atoms.

The symbol "$C_2$" means alcohols containing two carbon atoms.

The symbol "$C_{2+}$" means all alcohols containing two or more carbon atoms.

**The figures in Table 4 thus represent to percent of the indicated carbon number alcohols as a fraction of all the higher alcohols e.g. weight $C_2$ alcohol × 100 divided by weight of $C_{2+}$ alcohols.

TABLE 1

| | | Molar Ratio Hydrogen to Carbon Monoxide 1:1 | | | | | | | |
|---|---|---|---|---|---|---|---|---|---|
| Example Number | Catalyst From Example Number | Amount of Potassium in Catalyst Percent Weight | Weight Percent K Added* | Temperature °C. | Space Velocity v/v/hour | Liquid Product g/l/hour | Higher Alcohols Product g/l/hour | Alcohols/ Hydro- Carbons | Percent Higher Alcohols |
| 4 | 1 | 8.2 | 3 | 285 | 2400 | 159 | 31 | 7.4 | 19.4 |
| 5 | 2 | 8.7 | 3 | 285 | 2400 | 132 | 24 | 6.4 | 18.2 |
| 6 | 3 | 7.3 | 0 | 285 | 2400 | 254 | 40 | 4.0 | 15.7 |
| 7 | 1 | 8.2 | 3 | 300 | 2400 | 149 | 40 | 8.1 | 26.7 |
| 8 | 2 | 8.7 | 3 | 300 | 2400 | 133 | 32 | 6.1 | 24.3 |
| 9 | 3 | 7.3 | 0 | 300 | 2400 | 190 | 52 | 4.2 | 27.2 |
| 10 | 1 | 8.2 | 3 | 325 | 2400 | 130 | 55 | 8.8 | 42.2 |
| 11 | 2 | 8.7 | 3 | 325 | 2400 | 121 | 49 | 7.2 | 40.8 |
| 12 | 3 | 7.3 | 0 | 325 | 2400 | 138 | 52 | 4.0 | 38.1 |
| | | | Pressure in each case 100 psig | | | | | | |

*Added by impregnation to washed catalyst after calcination.

TABLE 2

| | | Molar Ratio Hydrogen to Carbon Monoxide 2:1 | | | | | | | |
|---|---|---|---|---|---|---|---|---|---|
| Example Number | Catalyst From Example Number | Amount of Potassium in Catalyst Percent Weight | Weight Percent K Added* | Temperature °C. | Space Velocity v/v/hour | Liquid Product g/l/hour | Higher Alcohols Product g/l/hour | Alcohols/ Hydro- Carbons | Percent Higher Alcohols |
| 13 | 3 | 7.3 | 0 | 200 | 9000 | 56 | 10 | — | 17.3 |
| 14 | 3 | 7.3 | 0 | 220 | 9000 | 117 | 10 | — | 8.6 |
| 15 | 3 | 7.3 | 0 | 240 | 9000 | 211 | 19 | — | 8.8 |
| | | | Pressure in each case 1000 psig | | | | | | |

The above results in Tables 1 and 2 show that potassium can be added by impregnation resulting in an active catalyst.

TABLE 3

Molar Ratio of Hydrogen:Carbon Monoxide 0.46:1

| Example Number | Catalyst From Example Number | Amount of Potassium in Catalyst Percent Weight | Weight Percent K Added* | Temperature °C. | Space Velocity v/v/hour | Liquid Product g/l/hour | Higher Alcohols Product g/l/hour | Alcohols/Hydro-Carbons | Percent Higher Alcohols |
|---|---|---|---|---|---|---|---|---|---|
| 16 | 1 | 8.2 | 3 | 285 | 9000 | 230 | 51 | 10.1 | 22.1 |
| 17 | 1 | 8.2 | 3 | 300 | 9000 | 264 | 82 | 11.4 | 31.0 |
| 18 | 1 | 8.2 | 3 | 325 | 9000 | 269 | 146 | 16.3 | 54.3 |

Pressure in each case 1000 psig

*Added by impregnation to washed catalyst after calcination.

The above results show that using a feed with a higher proportion of carbon monoxide yields a product having a higher proportion of higher alcohols and a higher ratio of higher alcohols to hydrocarbons.

TABLE 4

Height Percent on a Methanol-free Basis**

| Example Number | $C_2/C_{2+}$ | $C_3/C_{2+}$ | $C_4/C_{2+}$ | $C_5/C_{2+}$ | $C_6/C_{2+}$ |
|---|---|---|---|---|---|
| 4 | 48.9 | 32.9 | 12.9 | 5.3 | 0.0 |
| 5 | 52.6 | 34.9 | 12.4 | 0.0 | 0.0 |
| 6 | 26.3 | 34.7 | 18.9 | 9.8 | 9.7 |
| 7 | 35.1 | 44.2 | 10.7 | 7.4 | 2.5 |
| 8 | 33.6 | 42.1 | 14.5 | 7.1 | 2.8 |
| 9 | 21.9 | 35.6 | 23.4 | 10.6 | 8.4 |
| 10 | 16.7 | 53.4 | 16.5 | 9.9 | 3.6 |
| 11 | 16.9 | 55.3 | 19.1 | 4.9 | 3.7 |
| 12 | 15.6 | 38.6 | 28.8 | 10.0 | 6.9 |
| 13 | 17.0 | 37.3 | 25.7 | 12.3 | 7.6 |
| 14 | 41.3 | 33.8 | 15.1 | 5.8 | 3.9 |
| 15 | 53.3 | 25.7 | 16.0 | 4.9 | 0.0 |
| 16 | 45.6 | 36.5 | 8.5 | 6.6 | 2.8 |
| 17 | 33.1 | 43.3 | 11.8 | 8.2 | 3.6 |
| 18 | 17.1 | 51.9 | 17.2 | 10.1 | 3.6 |

The above results show that the alcohol compositions produced contained at least 46 percent by weight of methanol and that the ratio of $C_3$ to $C_4$ alcohols was at least 1.25.

Example 19 Preparation of Catalyst

The proportions of the reactants employed were chosen to correspond to a catalyst of the formula:

$$Cu_{1.5}UAl_{0.2}K_xO_y$$

100 g of $Cu(NO_3)_2 \cdot 2\frac{1}{2}H_2O$, 144 g of $UO_2(NO_3)_2 \cdot 6H_2O$ and 22.0 g of $Al(NO_3)_3 \cdot 9H_2O$ were dissolved in two liters of methanol. A two molar KOH in methanol solution was then added to the mixture over a period of one hour and 15 minutes until the pH was 7.0. The mixture was then vacuum filtered and the filter cake placed in a room temperature oven and slowly heated to 400° C. and calcined at that temperature for two hours. After cooling to room temperature the catalyst was then ground to a powder and dispersed in one liter of distilled water. The catalyst mixture was then vacuum filtered and the filter cake reslurried with one liter of distilled water and again vacuum filtered. The catalyst was then placed in an oven at 120° C. and dried over night. The catalyst was split into four portions. One portion was designated 19A. Catalyst 19A had the following analysis:

Cu 19 percent
U 51 percent
Al 1.2 percent
K 8.4 percent corresponding to a formula of $Cu_{1.4}UAl_{0.2}K_{1.0}O_y$. Another portion was doped by adding a solution of KOH in distilled water until an additioal 3 percent potassium $K^+$ was added. The doped catalyst was then dried in an oven at 120° C. The catalyst was pelletized with 3 percent graphite and designated 19B. Catalyst 19B had the following analysis:

Cu 17 percent
U 47 percent
Al 1.1 percent
K 10.0 percent corresponding to a formula of $Cu_{1.4}UAl_{0.2}K_{1.3}O_y$. A second portion of catalyst was doped by adding a solution of Na OH in distilled water until the added sodium level reached 1.5 percent. The doped catalyst was then dried in an oven at 120° C. and pelletized with 3 percent graphite and designated 19C. Catalyst 19C had the following analysis:

Cu 17 percent
U 46 percent
Al 1.1 percent
K 7.6 percent
Na 1.4 percent corresponding to a formula of $Cu_{1.4}UAl_{0.2}K_{1.0}Na_{0.3}O_y$. Another portion of the catalyst was doped by adding a solution of Cs OH in distilled water until the cesium level reached 9 percent. The doped catalyst was then dried in an oven at 120° C., pelletized with 3 percent graphite and designated 19D. Catalyst 19D had the following analysis:

Cu 16 percent
U 42 percent
Al 0.97 percent
K 6.7 percent
Cs 8.3 percent corresponding to a formula of $Cu_{1.4}UAl_{0.2}K_{1.0}Cs_{0.4}O_y$.

Example 20 Preparation of Catalyst

The proportions of the reactants employed were chosen to correspond to a catalyst of the formula $Cu_{1.5}UAl_{0.2}K_xO_y$.

The catalyst preparation of Example 19 was repeated exactly as far as the drying at 120° C. except the calcination was effected at 350° C. and the water washing was effected by reslurrying in two liters of distilled water once only.

A portion of this catalyst (26.70 g) was impregnated with a solution of KOH in distilled water until the added $K^+$ level reached 3 percent. The catalyst was then dried at 120° C. in an oven for two hours and pelletized with 3 percent graphite and designated Catalyst 20.

Example 21 Catalyst Preparation

The proportions of the reactants employed were chosen to correspond to a formula of $Cu_{1.5}UAl_{0.2}Ba_x$-$O_yK_z$ 50.0 g of $Cu(NO_3)_2.2\frac{1}{2}H_2O$, 72.26 g of $UO_2(NO_3)_2.6H_2O$ and 10.80 g of $Al(NO_3)_2.9H_2O$ were dissolved in one liter of methanol. 14.21 g of $BaCO_3$ was then added to the solution. A 2M solution of KOH in methanol was then added over a period of about one hour and 30 minutes until the pH was 9.90. The mixture was then vacuum filtered, the filtercake reslurried with one liter of methanol a vacuum filtered again. The solid was then placed in a room temperature furnace and slowly heated to 350° C. and calcined at that temperature for two hours and cooled to room temperature. The solid was ground to a powder and dissolved in one liter of distilled water. The solid was then vacuum filtered and the filtercake dried in an oven at 120° C. The finished material was designated Catalyst 21.

Analysis of Catalyst 21 was:
Cu 18 percent
U 48 percent
Al 1.0 percent
K 4.5 percent
Ba 6.7 percent
corresponding to a formula of: $Cu_{1.4}UAl_{0.18}K_{0.57}Ba_{0.24}O_y$.

The catalysts prepared in Examples 19, 20 and 21 were tested for activity and the results are summarized in Tables 5-8.

TABLE A

| | X-Ray Diffraction Data for Cu—U Catalysts | | | | | |
|---|---|---|---|---|---|---|
| | | Catalyst Number | | | | |
| | Compound | 19A | 19B | 19C | 19D | 21 |
| 7.01 A | K2 U4 O13 | na | na | 0 | 0 | 66 |
| 6.60 A | K2 U2 O7 | na | na | 135 | 130 | 16 |
| 3.78 A | K NO3 | 0 | 0 | 0 | 0 | 0 |
| 3.48 A | K2U4O13/CuUO4 | 45 | 45 | 45 | 43 | 100 |
| 3.37 A | Graphite | 10 | 110 | 105 | 80 | 0 |
| 3.28 A | K2U2O7/CuU3O10 | 100 | 100 | 100 | 100 | 15 |
| 3.12 A | K2U4O13 | 10 | 5 | 15 | 5 | 85 |
| 2.85 A | K2U2O7/CuU04 | 15 | 15 | 20 | 20 | 0 |
| 2.62 A | K2U2O7 | 3 | 3 | 2 | 5 | 5 |
| 2.53 A | CuO | 12 | 12 | 12 | 15 | 10 |
| 2.33 A | CuO | 15 | 13 | 15 | 15 | 18 |

TABLE A-continued

| | X-Ray Diffraction Data for Cu—U Catalysts | | | | | |
|---|---|---|---|---|---|---|
| | | Catalyst Number | | | | |
| | Compound | 19A | 19B | 19C | 19D | 21 |
| 2.19 A | K2U2O7 | 10 | 12 | 12 | 14 | 0 |
| 2.02 A | K2U2O7 | 20 | 25 | 25 | 30 | 21 |
| 1.92 A | K2U2O7/CuU04/CuU3O10 | 12 | 8 | 12 | 15 | 25 |
| 1.87 A | CuO | 2 | 2 | 2 | 2 | 15 |

The figures in the Table show the relative intensities of the x-ray lines. The strong lines at 6.60 A and 7.01 A show the presence of significant amount of (i) $K_2U_2O_7$ in Catalysts 19C and 19D and (ii) the presence of $K_2U_4O_{13}$ in Catalyst 21 respectively.

Since all the Catalysts 19A, 19B, 19C and 19D were prepared by the same technique (apart from the impregnation) it is concluded that they all contain potassium uranates.

The catalysts prepared in Examples 19, 20 and 21 were employed to make alcohols from synthesis gas. The reaction conditions and results are summarized in Tables 5-8.

TABLE 5

| Alcohol Synthesis Results Over Cu1.5-U—A10.2-Ax—Oy Catalysts | | | | | | |
|---|---|---|---|---|---|---|
| Example No. | 23 | 24 | 25 | 26 | 27 | 28 |
| Cat. No. | 19C | 19C | 19C | 19D | 19D | 19D |
| Temp °C. | 285.0 | 300.0 | 325.0 | 285.0 | 300.0 | 325.0 |
| Press psig | 1000.0 | 1000.0 | 1000.0 | 1000.0 | 1000.0 | 1000.0 |
| SV h-1 | 4800.0 | 4800.0 | 4800.0 | 4800.0 | 4800.0 | 4800.0 |
| CT sec | 26.9 | 26.2 | 25.1 | 26.9 | 26.2 | 25.1 |
| Time Hours | 2.0 | 2.0 | 2.0 | 2.0 | 2.0 | 2.0 |
| Liq Wt Grams | 5.3 | 5.0 | 4.1 | 4.3 | 3.1 | 1.5 |
| Percent C1OH | 72.3 | 59.2 | 39.5 | 81.3 | 72.7 | 54.8 |
| C2OH | 7.7 | 8.5 | 7.2 | 7.5 | 9.0 | 6.1 |
| n-C3OH | 4.3 | 8.3 | 16.1 | 7.4 | 10.7 | 9.3 |
| i-C3OH | 0.4 | 0.4 | 0.5 | 0.5 | 0.0 | 0.0 |
| n-C4OH | 2.5 | 3.4 | 3.4 | 1.9 | 2.8 | 1.7 |
| i-C4OH | 0.5 | 0.9 | 3.9 | 1.0 | 2.7 | 3.5 |
| n-C5OH | 0.4 | 0.5 | 0.6 | 0.4 | 0.7 | 0.0 |
| i-C5OH | 0.8 | 1.6 | 0.0 | 0.0 | 0.0 | 2.2 |
| n-C6OH | 0.2 | 0.3 | 0.4 | 0.0 | 0.6 | 0.8 |
| i-C6OH | 0.0 | 0.5 | 0.8 | 0.0 | 0.7 | 1.1 |
| Wt CH4 Grams | 0.1 | 0.2 | 0.2 | 0.1 | 0.1 | 0.1 |
| Wt CO2 Grams | 2.6 | 3.5 | 4.9 | 2.4 | 2.0 | 2.0 |
| C-BAL | 98.0 | 94.6 | 92.0 | 92.5 | 90.0 | 84.0 |
| Prod-g/l/hr | 264.0 | 249.0 | 204.0 | 213.0 | 155.0 | 74.0 |
| Prod-Hi Alc | 44.0 | 61.0 | 67.0 | 40.0 | 42.0 | 18.0 |
| HA/HC | 6.9 | 6.6 | 5.7 | 7.8 | 10.3 | 4.8 |

The molar ratio of hydrogen to carbon monoxide fed was 1:1 in all cases.

TABLE 6

| Alcohol Synthesis Results Over Cu1.5-U—A10.2-Ax—Oy Catalysts | | | | |
|---|---|---|---|---|
| Example No. | 29 | 30 | 31 | 32 |
| Cat. No. | 19B | 19B | 19B | 20 |
| Temp °C. | 285.0 | 300.0 | 325.0 | 275.0 |
| Press psig | 1000.0 | 1000.0 | 1000.0 | 1500.0 |
| SV h-1 | 4800.0 | 4800.0 | 4800.0 | 9000.0 |
| CT sec | 26.9 | 26.2 | 25.1 | 21.9 |
| Time Hours | 2.0 | 2.0 | 2.0 | 2.0 |
| Liq Wt Grams | 5.2 | 4.6 | 4.3 | 13.1 |
| Percent C1OH | 72.4 | 72.1 | 42.4 | 81.8 |
| C2OH | 8.1 | 10.3 | 7.2 | 5.0 |
| n-C3OH | 4.2 | 11.2 | 17.5 | 2.9 |
| i-C3OH | 0.4 | 0.0 | 0.5 | 0.0 |
| n-C4OH | 2.3 | 3.5 | 2.9 | 1.5 |
| i-C4OH | 0.4 | 1.3 | 5.2 | 0.0 |
| n-C5OH | 0.4 | 0.6 | 0.8 | 0.0 |
| i-C5OH | 0.8 | 0.0 | 3.2 | 0.0 |
| n-C6OH | 0.4 | 0.4 | 0.6 | 0.7 |
| i-C6OH | 0.0 | 0.6 | 0.9 | 0.4 |
| Wt CH4 Grams | 0.1 | 0.2 | 0.2 | 0.2 |

TABLE 6-continued

Alcohol Synthesis Results Over Cu1.5-U—A10.2-Ax—Oy Catalysts

| Example No. | 29 | 30 | 31 | 32 |
|---|---|---|---|---|
| Wt CO2 Grams | 2.4 | 3.6 | 5.0 | 3.0 |
| C-Bal | 93.3 | 95.1 | 94.5 | 91.7 |
| Prod-g/l/hr | 257.0 | 229.0 | 213.0 | 655.0 |
| Prod-Hi Alc | 43.0 | 64.0 | 83.0 | 69.0 |
| HA/HC | 6.7 | 7.1 | 7.7 | 6.5 |
| Hours on Stream | | | | 4.0 |

For Examples 29–31 the molar ratio of hydrogen to carbon monoxide fed was 1:1, for Examples 32–35 the ratio was 2:1.

TABLE 7

Alcohol Synthesis Results Over Cu1.5-U—A10.2-Ax—Oy Catalysts

| Example No. | 33 | 34 | 35 |
|---|---|---|---|
| Cat. No. | 21 | 21 | 21 |
| Temp °C. | 240.0 | 260.0 | 260.0 |
| Press psig | 1000.0 | 1000.0 | 1000.0 |
| SV h-1 | 9000.0 | 9000.0 | 36000.0 |
| CT sec | 15.6 | 15.0 | 3.8 |
| Time Hours | 1.0 | 1.0 | 1.0 |
| Liq Wt Grams | 2.5 | 7.7 | 2.8 |
| Percent C1OH | 91.3 | 91.5 | 90.6 |
| C2OH | 4.9 | 4.8 | 3.5 |
| n-C3OH | 0.7 | 1.1 | 0.7 |
| i-C3OH | 0.3 | 0.4 | 0.3 |
| n-C4OH | 0.1 | 0.4 | 0.2 |
| i-C4OH | 0.0 | 0.1 | 0.1 |
| n-C5OH | 0.0 | 0.1 | 0.0 |
| i-C5OH | 0.0 | 0.1 | 0.0 |
| n-C6OH | 0.0 | 0.0 | 0.0 |
| i-C6OH | 0.0 | 0.0 | 0.0 |
| Wt CH4 Grams | 0.1 | 0.1 | 0.1 |
| Wt CO2 Grams | 0.3 | 0.9 | 0.3 |
| C-Bal | 102.7 | 112.7 | 109.8 |
| Prod-g/l/hr | 252.0 | 771.0 | 1136.0 |
| Prod-Hi Alc | 16.0 | 57.0 | 58.0 |
| HA/HC | 2.9 | 6.2 | 2.5 |
| Hours on Stream | | | |

In the above Tables, the following abbreviations and terms mean:

| | |
|---|---|
| SV | means space velocity, in volumes of gas fed (carbon monoxide and hydrogen) per volume of catalyst per hour. |
| CT | means contact time in seconds of the reactant gas calculated at reaction conditions. |
| Time | is the duration of the product collection in hours. |
| Liq Wt | means the weight in grams of the liquid product collected. |
| Percent C1OH | means the weight percent of C1OH (methanol) in the liquid product. |
| C2OH | means ethanol. |
| i-C3OH | means isopropanol. |
| n-C3OH | means 1-propanol. |
| n-C4OH | means 1-butanol. |
| i-C4OH | means 2-methyl propanol. |
| n-C5OH | means 1-pentanol. |
| i-C5OH | means 2-methyl-1-butanol. |
| n-C6OH | means 1-hexanol. |
| i-C6OH | means 2-methyl-1-pentanol. |
| C-BAL is | $100 \times \frac{\text{moles of carbon recovered}}{\text{moles of carbon fed}}$ |
| Prod-g/l/hr | means productivity measured as grams of liquid per liter of catalyst per hour. |
| Prod-Hi Alc | means productivity of C2 and higher alcohols measured in grams per liter of catalyst per hour. |
| HA/HC | means the weight of C2 and higher alcohols divided by the weight of hydrocarbons. |

The above results in Tables 1–7 show that the catalysts containing copper and uranium according to the invention are active for the preparation of alcohols from syn gas.

TABLE 8

| Example Number | $C_2/C_{2+}$ | $C_3/C_{2+}$ | $C_4/C_{2+}$ | $C_5/C_{2+}$ | $C_6/C_{2+}$ |
|---|---|---|---|---|---|
| 23 | 46.1 | 28.3 | 17.7 | 6.6 | 1.4 |
| 24 | 34.9 | 35.5 | 17.7 | 8.5 | 3.3 |
| 25 | 21.9 | 50.5 | 21.9 | 1.9 | 3.9 |
| 26 | 40.1 | 42.2 | 15.6 | 2.1 | 0.0 |
| 27 | 32.9 | 39.9 | 20.2 | 2.5 | 4.9 |
| 28 | 24.6 | 37.8 | 21.2 | 8.8 | 7.7 |
| 29 | 47.7 | 27.2 | 16.2 | 6.6 | 2.3 |
| 30 | 36.9 | 40.2 | 17.1 | 2.1 | 3.7 |
| 31 | 18.6 | 46.4 | 20.8 | 10.3 | 3.9 |
| 33 | 79.4 | 16.6 | 2.9 | 1.0 | 0.0 |
| 34 | 69.5 | 20.6 | 7.2 | 2.6 | 0.0 |
| 35 | 73.1 | 19.9 | 5.6 | 1.5 | 0.0 |

The above results show that the alcohol composition produced contained at least 30 percent methanol and that the ratio of C3 to C4 alcohols was at least 1.25.

We claim:

1. A catalyst composition suitable for the conversion of mixtures of carbon monoxide and hydrogen to alcohols, said catalyst composition having the formula:

$$Cu_aUM_bA_cO_x$$

where M is one or more metals selected from the group consisting of Al, Pd, Mn, Cr, Fe, Co, Zn, Ce, V, Ru, Rh, Re, Os, Pt, Ir, Ag, Ti, La, and Zr; A is an alkali of alkaline earth metal or mixture thereof;

a is from 0.01 to 5.0;

b is a positive number up to 5.0;

c is a positive number up to 5.0 selected so that the catalyst composition contains more than 2% by weight of metal A; and x is a number such that the valence requirements of the other elements for oxygen are satisfied.

2. The catalyst composition as claimed in claim 1 wherein a is from 0.5 to 2.5.

3. The catalyst composition is claimed in claim 1 wherein b is a positive number up to 0.5.

4. The catalyst composition as claimed in claim 1 wherein c is from 0.5 to 2.0.

5. The catalyst composition as claimed in claim 1 containing from 5 to 20 percent by weight of metal A.

6. The catalyst composition as claimed in claim 1 wherein the composition is substantially free of anions other than oxide.

7. The catalyst composition as claimed in claim 1 which has been partially reduced by treatment with a reducing gas.

* * * * *